United States Patent
Ogunwobi et al.

(10) Patent No.: US 11,225,666 B2
(45) Date of Patent: Jan. 18, 2022

(54) PLASMID VECTOR FOR EXPRESSING A PVT1 EXON AND METHOD FOR CONSTRUCTING STANDARD CURVE THEREFOR

(71) Applicant: Research Foundation of the City University of New York, New York, NY (US)

(72) Inventors: Olorunseun O. Ogunwobi, Yonkers, NY (US); Gargi Pal, New York, NY (US)

(73) Assignee: Research Foundation of the City University of New York, New York, NY (US)

( * ) Notice: Subject to any disclaimer, the term of this patent is extended or adjusted under 35 U.S.C. 154(b) by 277 days.

(21) Appl. No.: 16/356,635

(22) Filed: Mar. 18, 2019

(65) Prior Publication Data

US 2019/0284565 A1    Sep. 19, 2019

Related U.S. Application Data

(60) Provisional application No. 62/644,023, filed on Mar. 16, 2018.

(51) Int. Cl.
*C12N 15/70* (2006.01)
*C12N 15/113* (2010.01)

(52) U.S. Cl.
CPC ............ *C12N 15/70* (2013.01); *C12N 15/113* (2013.01); *C12N 15/1135* (2013.01); *C12N 2310/141* (2013.01); *C12N 2800/101* (2013.01)

(58) Field of Classification Search
CPC .. C12N 15/70; C12N 15/113; C12N 15/1135; C12N 2800/101
See application file for complete search history.

(56) References Cited

U.S. PATENT DOCUMENTS

| | | | |
|---|---|---|---|
| 5,972,602 A | 10/1999 | Hyland et al. | |
| 10,344,283 B2* | 7/2019 | Ogunwobi | ......... C12N 15/1135 |
| 10,947,535 B2* | 3/2021 | Ogunwobi | ............ C12Q 1/686 |
| 2011/0287010 A1 | 11/2011 | Assinder et al. | |
| 2014/0065620 A1 | 3/2014 | Perez et al. | |
| 2017/0121711 A1 | 5/2017 | Ogunwobi et al. | |
| 2017/0130230 A1 | 5/2017 | Ogunwobi et al. | |

FOREIGN PATENT DOCUMENTS

CN    106754914 A  *  5/2017

OTHER PUBLICATIONS

Ilboudo, A. et al.; PVT1 Exon 9: A Potential Biomarker of Aggressive Prostate Cancer?; Int. J. Environ. Res. Public Health; Dec. 22, 2015; 13 pages; vol. 13, Issue 12.
Huppi, K. et al.; The 8q24 gene desert: an oasis of non-coding transcriptional activity; frontiers in Genetics; Apr. 2012; vol. 3, Article 69.
DDBJ; DNA Sequence Submission BC033263; Sep. 5, 2008.
Mammalian Gene Collection (MCG) Program Team; Generation and initial analysis of more than 15,000 full-length human and mouse cDNA sequences; PNAS; Dec. 24, 2002; pp. 16899-16903; vol. 99, No. 26.
Das, D. et al.; miR-1207-3p is a Novel Prognostic Biomarker of Prostate Cancer1; Translational Oncology; Jun. 2016; pp. 236-241; vol. 9 No. 3.
Das, D. et al.; miR-1207-3p regulates the androgen receptor in prostate cancer via FNDC1/fibronectin; Experimental CellResearch; Sep. 29, 2016; pp. 190-200; vol. 348; Elsevier Inc.
Das, D. et al.; Abstract 1074: A novel synthetic biotinylated microRNA-1207-3p duplex targets the 3'TUR of FNDC1 and inhibits proliferation and migration of prostate cancer cells; Molecular and Cellular Biology, Genetics; Jul. 2016; 2 pages.
Meyer, K. et al.; A Functional Variant at a Prostate Cancer Predisposition Locus at 8q24 is Associated with PVT1 Expression; PLOS Genetics; 11 pages; Jul. 2011; vol. 7, Issue 7.
THERMOFISHER; TaqMan Assay Hs0041303Q_m1, available at https:/lwww.thermofisher.com/order/genome-database/?pearUXVerSuffix=pearUX2&elcano Form=true#!/ge/assays/ge_all/?keyword = Hs00413039&searchMethod=keyword, accessed Feb. 25, 2019.

* cited by examiner

*Primary Examiner* — Iqbal H Chowdhury
(74) *Attorney, Agent, or Firm* — Peter J. Mikesell; Schmeiser, Olsen & Watts, LLP

(57) ABSTRACT

A method for cloning an exon into a plasmid vector. Exons related to prostate cancer (PVT1 exon 9, PVT1 exon 4A or PVT1 exon 4B) and miRNAs (miR-1205 or miR-1207-3p) are transformed into the plasmid vector. The cloned exons or miRNAs are linearized and their concentrations quantified. Serial dilutions in conjunction with spectroscopy permit the construction of a standard curve that permits absolute quantification of the exons or miRNAs in a biological sample from a patient.

15 Claims, 9 Drawing Sheets

Specification includes a Sequence Listing.

PLASMID VECTOR FOR EXPRESSING A PVT1 EXON AND METHOD FOR CONSTRUCTING STANDARD CURVE THEREFOR

CROSS-REFERENCE TO RELATED APPLICATIONS

This application claims priority to and is a non-provisional of U.S. Patent Application 62/644,023 (filed Mar. 16, 2018), the entirety of which is incorporated herein by reference.

STATEMENT OF FEDERALLY SPONSORED RESEARCH OR DEVELOPMENT

This invention was made with government support under grant number 8 G 12 MD007599 awarded by the National Institute of Health. The government has certain rights in the invention.

REFERENCE TO A SEQUENCE LISTING

This application contains a Sequence Listing in computer readable form. The computer readable form is incorporated herein by reference.

BACKGROUND OF THE INVENTION

Prostate cancer is the most common non-cutaneous cancer and the second leading cause of cancer-related death for men in the U.S. African Americans have the highest incidence of prostate cancer in the world, with an annual average of 229 per 100,000 men for the period of 2006-2010, which represents about two-fold more than Caucasian Americans. Prostate cancer is also the leading cancer in terms of incidence and mortality in men from Africa and the Caribbean. Consequently, African ancestry is a very important risk factor.

Prostate cancer is a heterogeneous disease, with multiple risks factors. The specific reasons for poor outcomes from prostate cancer in males of African ancestry (MoAA) when compared to Caucasian males (CM) are not understood. However, it is widely believed that the causes of prostate cancer disparities are complex and multifaceted. Two potential reasons are frequently proposed to explain this profound disparity in prostate cancer: (1) MoAA present more often than CM with advanced incurable prostate cancer due to more limited access to health care; (2) prostate cancer is biologically more aggressive in MoAA than CM, and can be attributed to environmental and/or genetic risk factors.

The 8q24 human chromosomal region is one of the most important susceptibility genetic loci for prostate cancer. Several studies have identified single nucleotide polymorphisms (SNPs) located in chromosome 8q24 as susceptibility markers for prostate cancer. The 8q24 chromosomal region has only one protein-coding gene, the well-known MYC oncogene implicated in different cancers, including prostate cancer. However, it also has a number of non-protein coding genes (such as PVT1) whose functional roles have not been thoroughly investigated yet.

In recent years, non-protein coding RNAs (ncRNAs) have received special attention because they have been identified in many studies as being important in cancer biology. Substantial progress has been made in understanding the role of small non-coding RNAs such as microRNAs (miR-NAs) in the development and progression of cancers. However, studying the role of long non-coding RNAs (nncRNAs) in cancers appears to be more complicated. LncRNAs are defined as endogenous cellular RNAs that have a size of more than 200 nucleotides and that do not possess an extended open reading frame. PVT1 exon 9, PVT1 exon 4A and PVT1 exon 4B are overexpressed in aggressively tumorigenic prostate cancer cell lines and prostate tumor tissues. Additionally, several miRNAs (e.g. miR-1205, and miR-1207-3p) are also known for treating prostate cancer.

The discussion above is merely provided for general background information and is not intended to be used as an aid in determining the scope of the claimed subject matter.

BRIEF DESCRIPTION OF THE INVENTION

A method for cloning an exon into a plasmid vector. Exons related to prostate cancer (PVT1 exon 9, PVT1 exon 4A or PVT1 exon 4B) and miRNAs (miR-1205 or miR-1207-3p) are transformed into the plasmid vector. The cloned exons or miRNAs are linearized and their concentrations quantified. Serial dilutions in conjunction with spectroscopy permit the construction of a standard curve that permits absolute quantification of the exons or miRNAs in a biological sample from a patient.

In a first embodiment, a method for cloning an exon into a plasmid vector is provided. The method comprising: ligating the exon into a plasmid vector, wherein the exon consists of: (1) a mature strand, and a corresponding complementary strand, wherein the mature strand is selected from a group consisting of PVT1 exon 9 (SEQ ID NO: 1), PVT1 exon 4A (SEQ ID NO: 2), PVT1 exon 4B (SEQ ID NO: 3), or (2) a miRNA selected from a group consisting of miR-1205 (SEQ ID NO: 7), and miR-1207-3p (SEQ ID NO: 8); transforming the plasmid vector into *Escherchia coli* (*E. coli*); selecting at least one colony of the *Escherchia coli* (*E. coli*) that successfully transformed the plasmid vector into the *Escherchia coli* (*E. coli*).

In a second embodiment, a plasmid vector is provided. The plasmid vector comprising: a vector comprising: DNA segment selected from a group consisting of PVT1 exon 9 (SEQ ID NO: 1), PVT1 exon 4A (SEQ ID NO: 2) and PVT1 exon 4B (SEQ ID NO: 3); and a corresponding complementary strand.

In a third embodiment, the plasmid vector is provided. The plasmid vector comprising: a vector consisting of: a RNA segment selected from a group consisting of miR-1205 (SEQ ID NO: 7) and miR-1207-3p (SEQ ID NO: 8); a complementary strand corresponding to the RNA segment; and SEQ ID NO: 6 and a corresponding complementary strand.

This brief description of the invention is intended only to provide a brief overview of subject matter disclosed herein according to one or more illustrative embodiments, and does not serve as a guide to interpreting the claims or to define or limit the scope of the invention, which is defined only by the appended claims. This brief description is provided to introduce an illustrative selection of concepts in a simplified form that are further described below in the detailed description. This brief description is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

So that the manner in which the features of the invention can be understood, a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the invention encompasses other equally effective embodiments. The drawings are not necessarily to scale, emphasis generally being placed upon illustrating the features of certain embodiments of the invention. In the drawings, like numerals are used to indicate like parts throughout the various views. Thus, for further understanding of the invention, reference can be made to the following detailed description, read in connection with the drawings in which.

DETAILED DESCRIPTION OF THE INVENTION

This disclosure provides an absolute quantification assay for PVT1-derived transcripts in biological samples such as tissue, urine, plasma, saliva. There is currently no absolute quantification assay for any PVT1-derived transcript.

Figure 1:
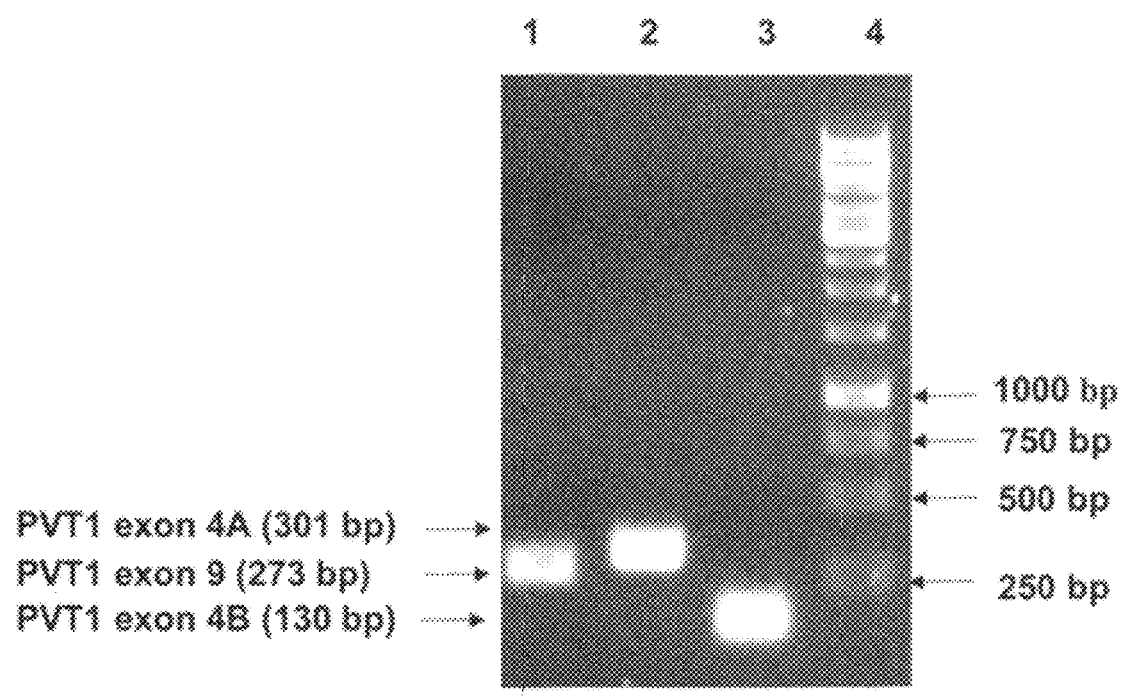
FIG. 1 depicts a gel electrophoresis showing a polymerase chain reaction showing PVT1 exon 9, PVT1 exon 4A, PVT1 exon 4B products. Lane 1—PVT1 exon 9, lane 2—PVT1 exon 4A, lane 3—PVT1 exon 4B, lane 4—ladder (1 kb)

This disclosure provides expression vectors that can be used as standards to create a standard curve for absolute quantification in the detection of PVT1 exon 9 (SEQ ID NO: 1), PVT1 exon 4A (SEQ ID NO: 2), PVT1 exon 4B (SEQ ID NO: 3), and miR-1205 (SEQ ID NO: 7), and miR-1207-3p (SEQ ID NO: 8). Primers were designed for the amplification of PVT1 exon 9 (273 bp), PVT1 exon 4A (301 bp), and PVT1 exon 4B (130 bp) and PCR was performed with those gene-specific primers. The PCR product was run in 1% agarose gel (FIG. 1). For cloning of PVT1 exon 9 (SEQ ID NO: 1), PVT1 exon 4A (SEQ ID NO: 2), and PVT1 exon 4B (SEQ ID NO: 3) transcripts two different plasmid vectors pGEM®-T Easy (SEQ ID NO: 4) and pcDNA3.1 (SEQ ID NO: 5) were chosen. The reader should appreciate the aforementioned exons are double stranded and include both the identified SEQ ID Nos and the corresponding complementary strand.

In one embodiment, plasmid vectors containing PVT1 exon 4A, PVT1 exon 4B, PVT1 exon 9, and miR-1205 and miR-1207-3p are used as standards in absolute quantification assays that determine absolute amounts of these transcripts in biological samples (including but not limited to tissue, blood, and urine samples). Absolute quantification of PVT1 exon 4A, PVT1 exon 4B, and PVT1 exon 9, and miR-1205 and miR-1207-3p is performed using the engineered plasmid vectors containing the transcripts. This enables determination of a range of quantities characteristic of normal healthy people, a range of quantities characteristic of benign prostatic hyperplasia, and a range of quantities characteristic of prostate cancer. Plasmid vectors containing PVT1 exon 4A, PVT1 exon 4B, and PVT1 exon 9, and miR-1205 and miR-1207-3p are also useful for discovery of the functional and molecular mechanisms of action of PVT1 exon 4A, PVT1 exon 4B, and PVT1 exon 9, miR-1205 and miR-1207-3p. In addition, plasmid vectors containing miR-1205 and miR-1207-3p can be used as a therapeutic strategy in prostate cancer.

Initial attempts failed to clone these small fragments. Cloning of the PVT1 exons has proven to be so difficult that this is the first report of successful cloning. In some attempts no band was formed in the corresponding electrophoresis gel. In other attempts, bands were present in the electrophoresis but these bands did not correspond to the correct size. In some attempts, but bands corresponded to the correct size but, after sequencing, several bases were determined to be missing. To address these failures, adjustments were made at several key steps in the cloning procedure: Specifically, customized primer sequences (see Table 1) were used. In case of pGEM-T, a blunt end cloning approach was used. A-tailing generated an A overhang, which increased the efficiency of cloning. In case of pcDNA3.1, restriction enzymes were used (e.g. 1 hr, 2 hr digestions and also overnight). Different ratios of vector and insert were used. Specific temperatures (18, 22, 25° C.) and time duration (1 hr, 2 hrs, overnight) of ligation was also used.

Figure 2:
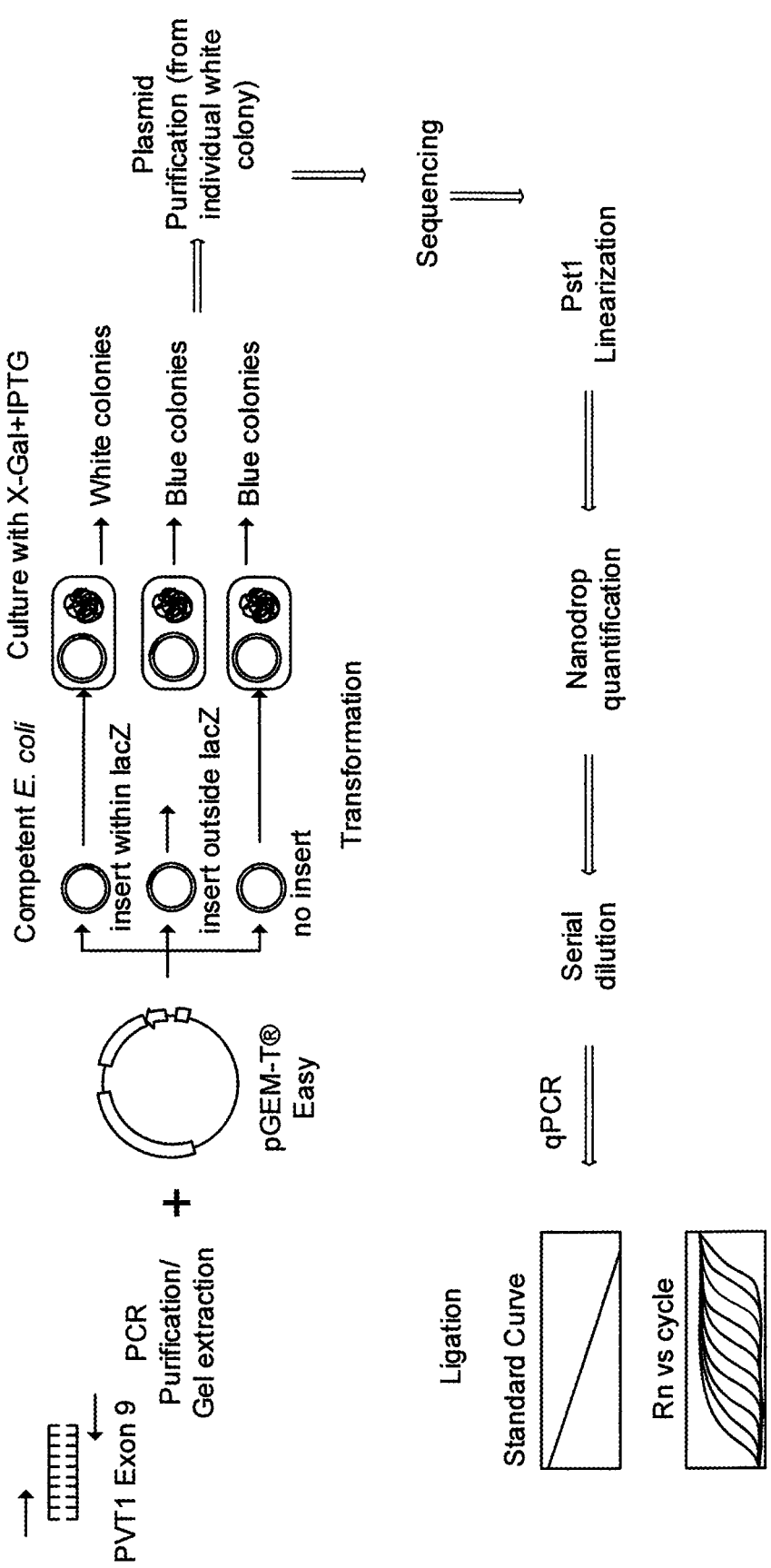
FIG. 2 is a schematic representation of cloning in pGEM®-T Vector.

Cloning strategy: The plasmid pGEM®-T Easy (SEQ ID NO: 4) was used as a cloning vector. The pGEM®-T Easy vector (Promega, New York, USA) is a pre-linearized vector where a dT residue has been added to the 3' end of the vector, allowing for what is referred to as TA cloning. The DNA fragment to be cloned can contain a poly-A tail at both ends (FIG. 2). The pGEM(R)-T Easy Vector (SEQ ID NO: 4) has been linearized with EcoRV at Base 60 of this sequence and a T added to both 3'-ends. The additional T is not included in SEQ ID NO: 4.

The 273 bp PVT1 exon 9 fragment (SEQ ID NO: 1) was synthesized and the dsDNA was reconstituted and amplified with polymerase chain reaction (PCR). Thermostable DNA polymerases with proofreading activity (Phusion High-Fidelity DNA Polymerase), was used to generate blunt-ended fragments. To increase the efficiency, PCR product was modified using the A-tailing procedure. The purified product was ligated (overnight at 4° C.) to pGEM®-T Easy vector (SEQ ID NO: 4) and then transformed in *E. coli* JM109 strain. LB/ampicillin/IPTG/X-Gal plates were used for transformation and screening of clones.

Figure 3:
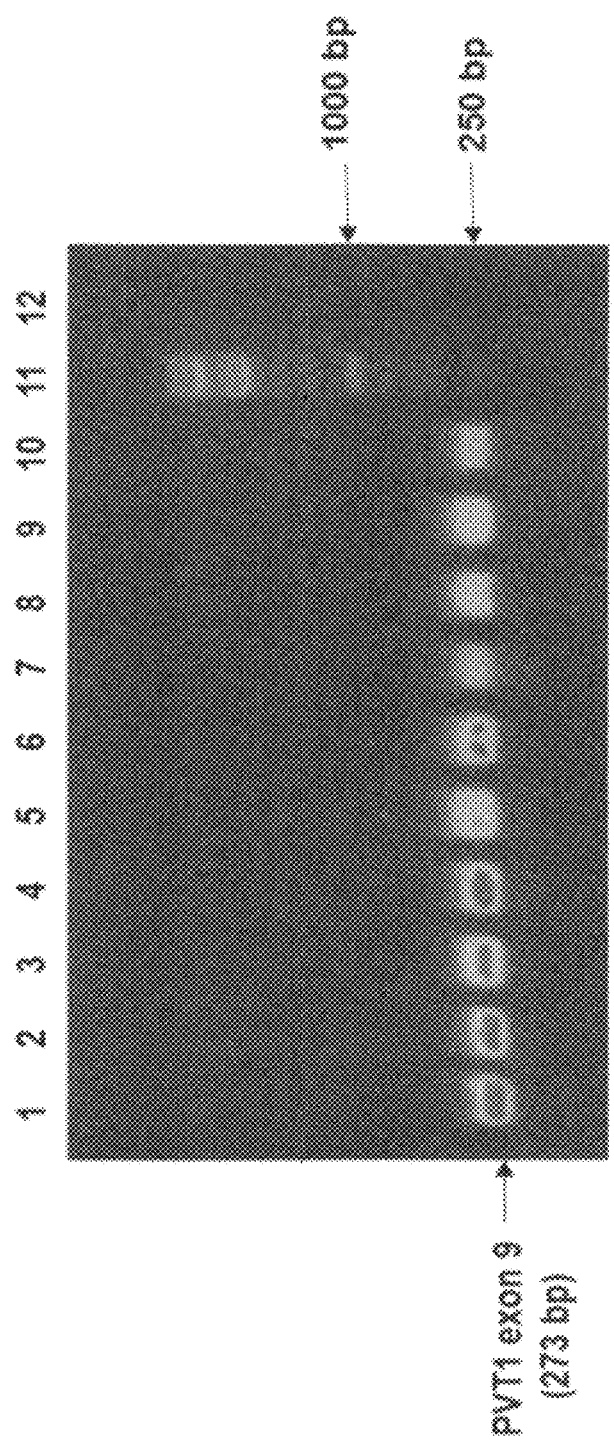
FIG. 3 is a gel electrophoresis depicting colony PCR showing the presence of pGEM-T-PVT1 exon 9 insert (273 bp). (Positive clones are present in lane 1-10, no insert is present in lane 12, lane 11—1 kb ladder)

The pGEM®-T Easy vector (SEQ ID NO: 4) is a high-copy-number vector containing T7 and SP6 RNA polymerase promoters flanking a multiple cloning region within the α-peptide coding region of the enzyme β-galactosidase. Insertional inactivation of the α-peptide allows identification of recombinants by blue/white screening on indicator plates. White colonies appearing in plates are expected to have inserts. The white colonies were screened through colony PCR using the same set of primers. The PCR products were run in gel (FIG. 3). Most of the clones were found to be positive for PVT1 exon 9 (SEQ ID NO: 1) as the band of correct size (273 bp) was present in almost all the lanes (except lane 12).

Figure 4:
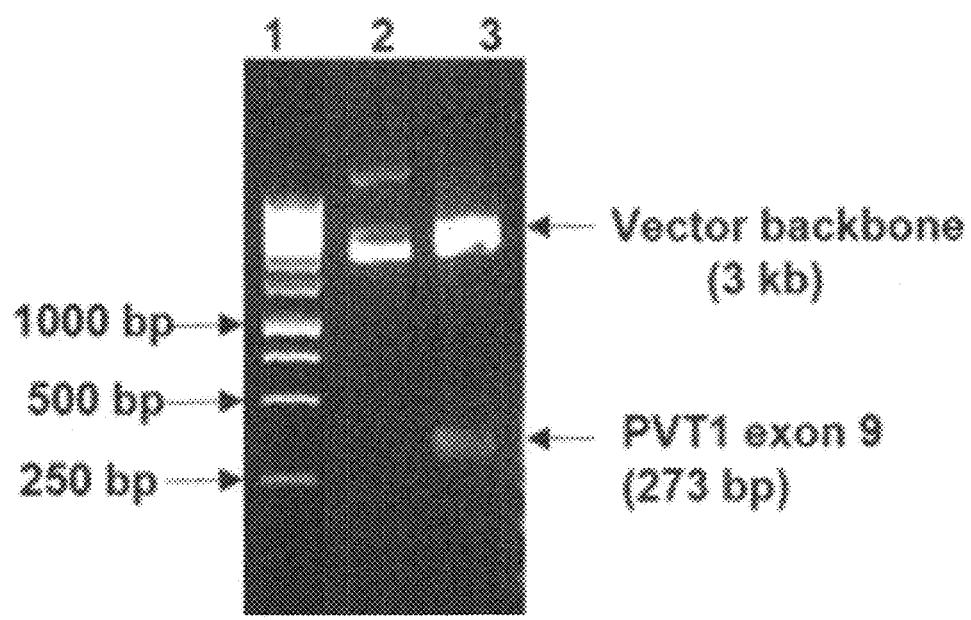
FIG. 4 is a gel electrophoresis depicting confirmation of pGEM-T-PVT1 exon 9 clone through restriction digestion. (Lane 1—1 kb ladder, lane 2—undigested plasmid, lane 3—digested plasmid showing pGEM-T vector backbone and PVT1 exon 9 insert (273 bp))

The plasmid DNA was isolated from some of these colonies and the presence of insert was confirmed with restriction digestion (FIG. 4). The pGEM®-T Easy Vector (SEQ ID NO: 4) multiple cloning region is flanked by recognition sites for the restriction enzymes EcoRI, BstZI and NotI, providing three single-enzyme digestions for release of the insert. NotI restriction enzyme was used to release the insert. Finally, the positive clones were confirmed by sequencing using SP6 and T7 promoter.

In the next step, cloned plasmid is linearized with PstI. Absolute quantitation can then be used to determine the exact number of DNA copies for estimating PVT1 exon 9 (SEQ ID NO: 1). A range of serial dilutions of the cloned vectors are prepared with a range flanking the anticipated quantities (e.g. $2\times10^3$ to $2\times10^9$ copies per ml). The concentration is measured spectrophotometrically by, for example, using a NANODROP®. The nanograms per microliter measured concentrations can be converted into copies per microliter by using the following equations:

$$\left(\left(\frac{x \text{ ng}}{\mu L \times 10^{-9}}\right)(bps \text{ in vector and exon}\times 660)\right)(6.022\times 10^{23}) = y \text{ copies}/\mu L$$

Using linear regression, a standard curve is constructed and used to convert copies/ml to standard international units (IU/ml). Similar strategy can be followed for PVT1 exon 4A (SEQ ID NO: 2), PVT1 exon 4B (SEQ ID NO: 3), miR-1205 (SEQ ID NO: 7), and miR-1207-3p (SEQ ID NO: 8).

Use of the plasmid pcDNA3.1 (SEQ ID NO: 5) as a cloning vector

Figure 5:
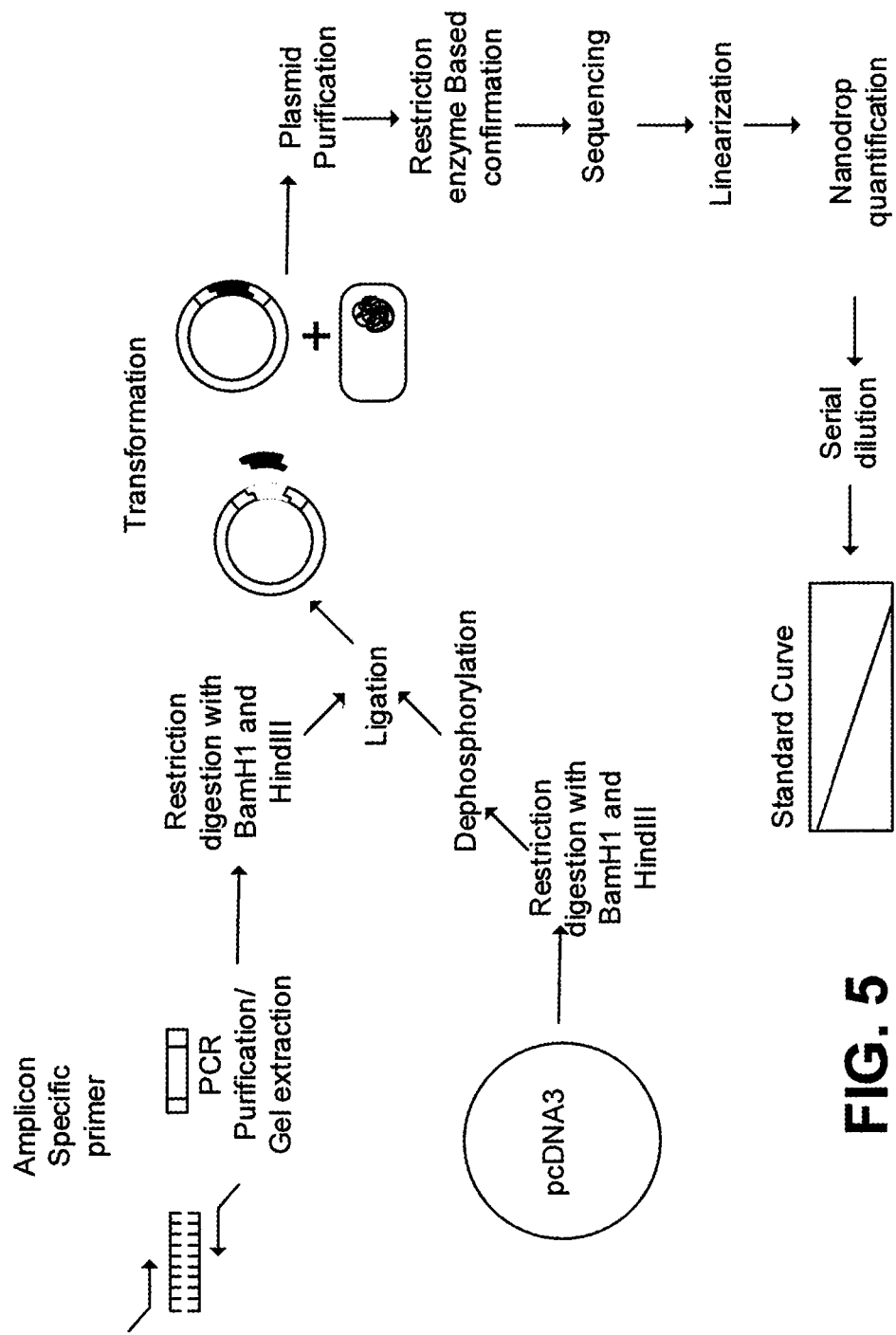
FIG. 5 is a schematic representation of cloning in pcDNA3.1 Vector.

In the next strategy, pcDNA3.1 (SEQ ID NO: 5) (ThermoFisher, New York, USA) is used as the vector which presents the double advantage over pGEM®-T Easy (SEQ ID NO: 4) of (1) being a powerful mammalian expression vector, and (2) allowing for directional cloning of the DNA fragment via cohesive-end restriction cloning (FIG. 5). For this experiment, another set of primers were designed as follows:

TABLE 1

PVT1 exon 9 p-GEMT Forward primer
(SEQ ID NO: 16)
5' GTT TTT TGC ATG TCT GAC ACC 3'

PVT1 exon 9 P-GEMT reverse primer
(SEQ ID NO: 9)
5' AGTAGAAAAAGAATTTAATAG 3' pcDNA3.1 exon 9 PCDNA Forward primer
(SEQ ID NO: 10)
5' att <u>AAGCTT</u> GTT TTT TGC ATG TCT GAC ACC 3' pcDNA 3.1 exon 9 PCDNA Reverse primer
(SEQ ID NO: 11)
5' att <u>GGATCC</u> AGTAGAAAAAGAATTTAATAG 3' pcDNA 3.1 exon 4A PCDNA Forward primer
(SEQ ID NO: 12)
5' att<u>AAGCTT</u>AGTCTCACTCTGTGGTCCAGG 3' pcDNA3.1 exon 4A PCDNA Reverse primer
(SEQ ID NO: 13)
5' att<u>GGATCC</u>CTGGACTCTTCAAAAATGTCA 3' pcDNA3.1 exon 4B PCDNA Forward primer
(SEQ ID NO: 14)
5' Att<u>AAGCTT</u>AATCCTGTTACACCTGGGATT 3' pcDNA3.1 exon 4B PCDNA Reverse primer
(SEQ ID NO: 15)
5' att<u>GGATCC</u>CTTAATTCTCCAATCTCAAAA 3'

The forward primer contains HindIII and the reverse primer contains BamHI restriction sites, respectively. These two restriction sites also occur in the pcDNA3.1 vector multiple cloning sites (MCS), HindIII at the 5' end and BamHI at the 3'end, but not elsewhere in the insert or vector.

Figure 6:
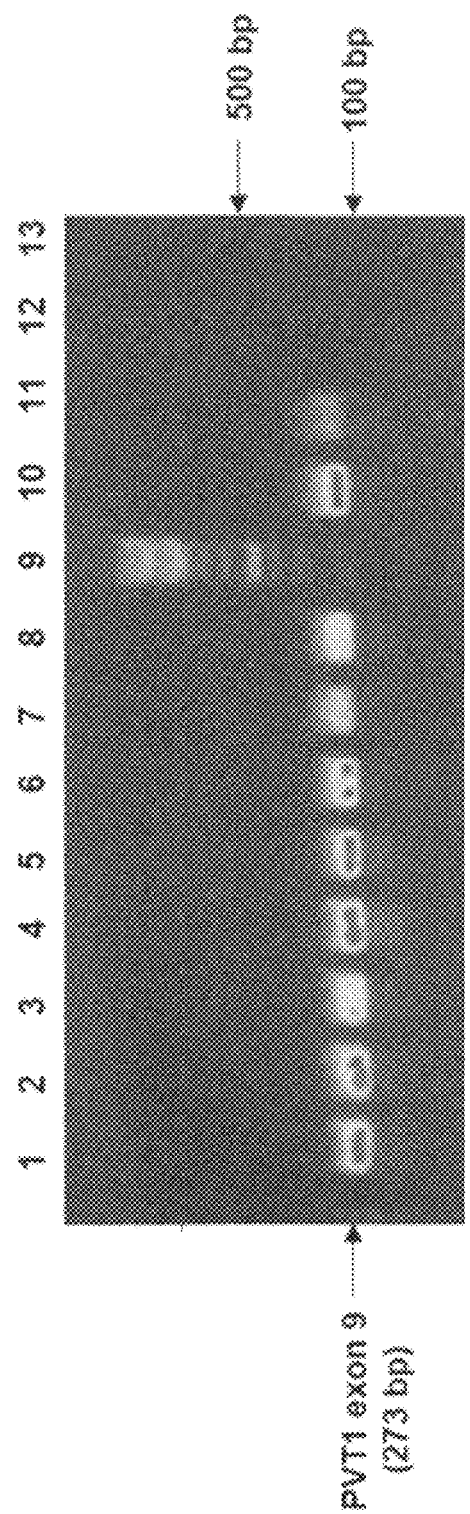
FIG. 6 is a gel electrophoresis of a colony PCR showing the presence of pcDNA-PVT1 exon 9 insert (273 bp). (Positive clones are present in lane 1-8, 10, 11, no insert is present in lane 12, lane 9—1 kb ladder, lane 13—blank)

The 273 bp PVT1 exon 9 (SEQ ID NO: 1) synthesized fragment was PCR amplified with these primers. The purified product was digested with HindIII and BamH1. The pcDNA3.1 vector was digested with the same set of enzymes and then dephosphorylated to avoid the chances of self-ligation. In the next step, digested vector and insert were purified (Qiagen kit) to remove all enzymes. The insert was ligated (25° C. for 2 hrs) into the plasmid, and the ligated plasmid was transformed into *E. coli* JM109 strain. Ampicillin was used as the selection marker. The transformants were screened through colony PCR (FIG. 6). Positive clones are present in lane 1-8, 10 and 11. No insert is present in lane 12 or lane 9 (1 kb ladder). Lane 13 is a blank.

Figure 7:
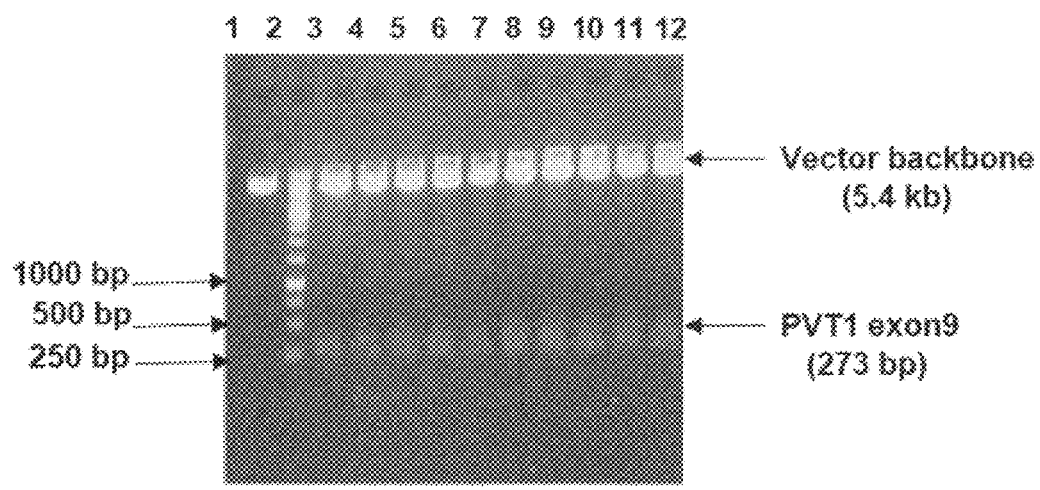
FIG. 7 is a gel electrophoresis depicting confirmation of pcDNA-PVT1 exon 9 clones through restriction digestion. (Lane 1—pcDNA3 vector digested with BamH1 and HindIII, lane 2—DNA Ladder (1 kb), lane (3-12)—Positive clones digested with BamH1 and HindIII showing vector backbone and PVT1 exon 9 insert (273 bp))

The plasmid DNA was isolated from the transformants showing bands in colony PCR. Presence of insert was also confirmed by digestion with restriction enzymes HindIII and BamHI (FIG. 7).

The positive clones were confirmed by sequencing (Eton Biosciences). The same strategy may be followed for miR-1205 (SEQ ID NO: 7) and miR-1207-3p (SEQ ID NO: 8). Once the recombinant vector is created, cloning in a prokaryotic system follows, as for pGEM®-T Easy (SEQ ID NO: 4), and the same steps can be used toward the absolute quantification of PVT1 exon 9 (SEQ ID NO: 1), PVT1 exon 4A (SEQ ID NO: 2), PVT1 exon 4B (SEQ ID NO: 3), miR-1205 (SEQ ID NO: 7), and miR-1207-3p (SEQ ID NO: 8). With a known absolute amount of the standard, one can assess for PVT1 exon 9 (SEQ ID NO: 1), PVT1 exon 4A (SEQ ID NO: 2), PVT1 exon 4B (SEQ ID NO: 3), miR-1205 (SEQ ID NO: 7), and miR-1207-3p (SEQ ID NO: 8) absolute quantity in any patient sample.

Figure 8:
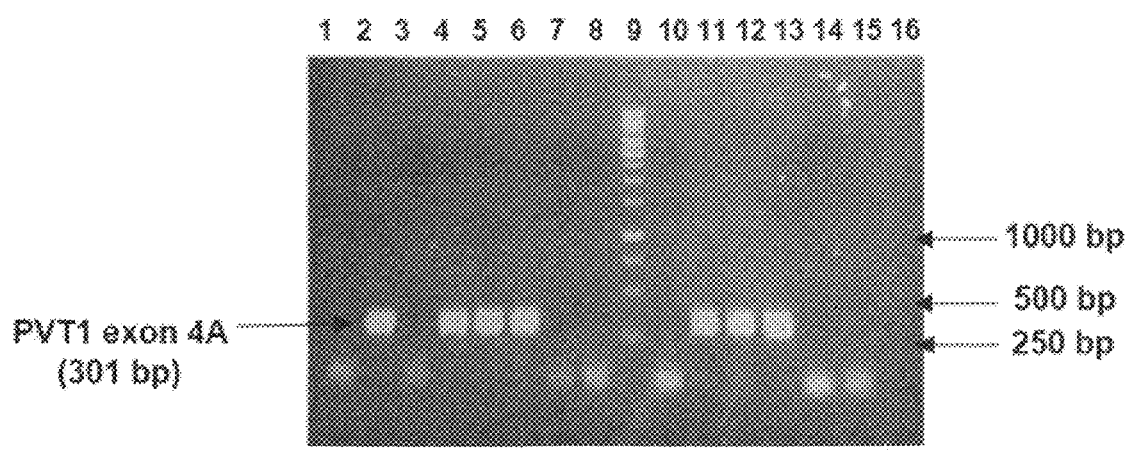
FIG. 8 is a gel electrophoresis depicting a colony PCR showing the presence of pcDNA-PVT1 exon 4A insert (301 bp) (Positive clones are present in lane 2, 4-6, 11-13, no insert is present in lane 1, 3, 7, 8, 10, 14, 15, lane 9—1 kb ladder, lane 16—blank)
Figure 9:
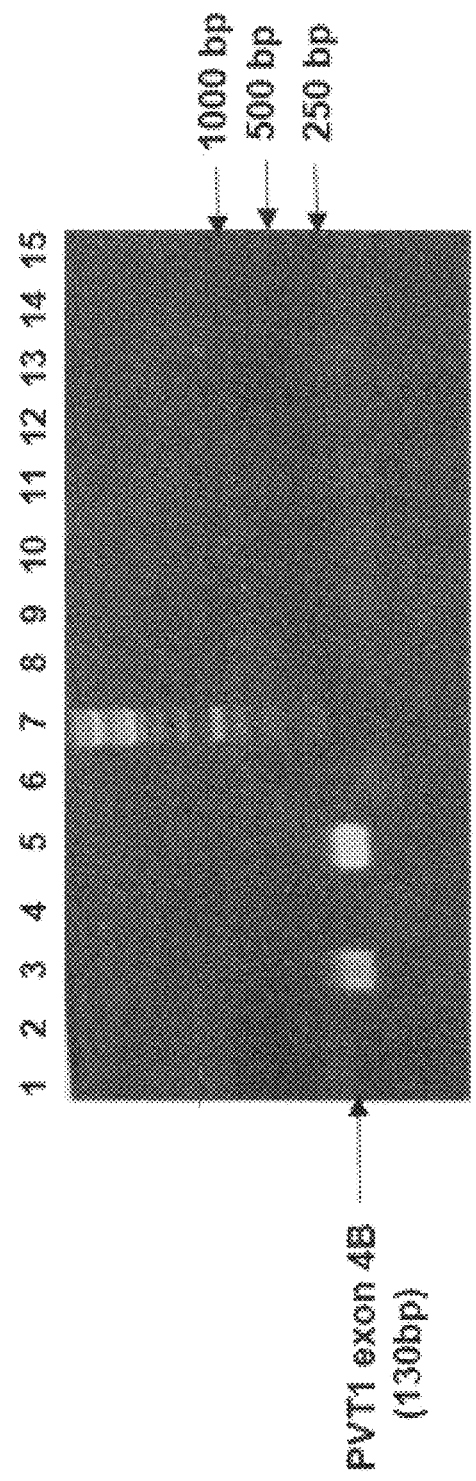
FIG. 9 is a gel electrophoresis depicting a colony PCR showing the presence of pcDNA-PVT1 exon 4B insert (130 bp). (Positive clones are present in lane 3 and 5, no insert is present in lane 1, 2, 4, 6, 8-14, lane 7—1 kb ladder, Lane 15—blank)
Figure 10:
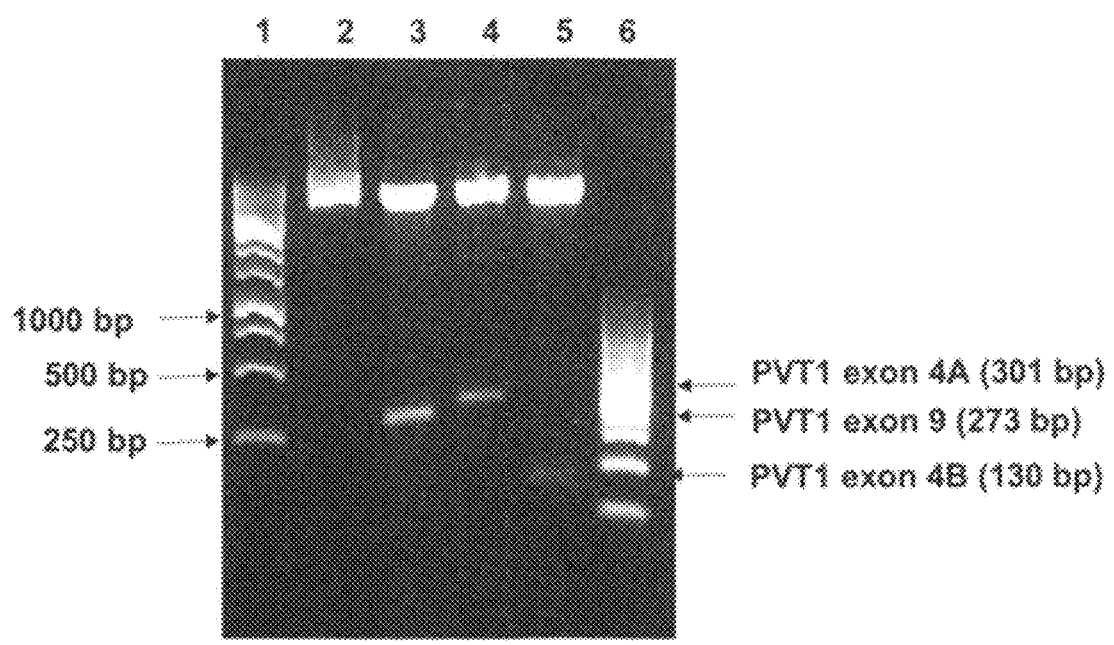
FIG. 10 is a gel electrophoresis depicting confirmation of pcDNA3.1-PVT1 exon 9, 4A, 4B clones through restriction digestion. (Lane 1—1 kb ladder, lane 2—vector backbone without insert, lane 3, 4, 5—digested plasmid showing pcDNA3.1 vector backbone and PVT1 exon 9 (273 bp), exon 4A, exon 4B, respectively, lane 6—100 bp ladder).

The second plasmid pcDNA3.1 (SEQ ID NO: 5) has an advantage over pGEM-T® (SEQ ID NO: 4) as this plasmid allows for a directional insertion of PVT1 exon 9 (SEQ ID NO: 1) and miR-1207-3p (SEQ ID NO: 7) via cohesive-end cloning. Therefore, this plasmid was chosen for the cloning of PVT1 exon 4A (SEQ ID NO: 2) and PVT1 exon 4B (SEQ ID NO: 3). PVT1 exon 4A (SEQ ID NO: 2) and PVT1 exon 4B (SEQ ID NO: 3) were cloned in pcDNA3.1 (SEQ ID NO: 5). The positive clones were selected through colony PCR (FIG. 8 and FIG. 9). The plasmid DNA was isolated from some of these colonies and the presence of insert was confirmed with restriction digestion (FIG. 10).

The PVT1 exon 9 (SEQ ID NO: 1), PVT1 exon 4A (SEQ ID NO: 2), PVT1 exon 4B (SEQ ID NO: 3) and miR-1207-3p (SEQ ID NO: 8) expression vectors may be used as standards to create a standard curve for absolute quantification in the detection of PVT1 exon 9 (SEQ ID NO: 1), PVT1 exon 4A (SEQ ID NO: 2), PVT1 exon 4B (SEQ ID NO: 3) and miR-1207-3p (SEQ ID NO: 8). Biological tissues (urine, plasma, saliva) of non-PCa and PCa patients can be assayed to determine the normal and abnormal changes for PVT1 exon 9 (SEQ ID NO: 1), PVT1 exon 4A (SEQ ID NO: 2), PVT1 exon 4B (SEQ ID NO: 3), miR-1205 (SEQ ID NO: 7), and miR-1207-3p (SEQ ID NO: 8).

Cloning of miR-1205 (SEQ ID NO: 7) and miR-1207-3p (SEQ ID NO: 8)

For cloning of miR-1205 and miR-1207-3p, miRNASelect™ pEGP-miR cloning and expression vector (Cell Biolabs) (SEQ ID NO: 6) was selected, which can clone and express an individual miRNA precursor in its native context while preserving putative hairpin structures to ensure biologically relevant interactions with endogenous processing machinery and regulatory partners, leading to properly cleaved microRNAs. BamHI and NheI sites can be used for this cloning. The miRNA cloning and expression vector was provided as bacterial glycerol stock. Individual colonies are obtained by culturing in an LB-ampicillin plate. The next step is transfection into target cells with the help of Lipofectamine 2000 (Invitrogen) and selection of stable clones by green fluorescence sorting or Puromycin resistance in 1-10 μg per mL Puromycin-containing medium.

PVT1 exon 9 (SEQ ID NO: 1), PVT1 exon 4A (SEQ ID NO: 2), PVT1 exon 4B (SEQ ID NO: 3), miR-1205 (SEQ ID NO: 7), and miR-1207-3p (SEQ ID NO: 8) expression vectors can be used in in vitro and in vivo studies to determine the molecular and functional effects of PVT1-derived transcripts in prostate cancer, breast cancer, cervical cancer, colon cancer, and any other diseases in which PVT1 is implicated.

Surprisingly, the inserts could be verified after digestion PCR, and sequencing of the inserts. Prior to the present disclosure, it was unclear if one could confirm the presence of the inserts either via PCR or sequencing. This disclosure confirms successful cloning into the vectors via both PCR and sequencing. The plasmid vectors expressing PVT1 exon 4A (SEQ ID NO: 2), PVT1 exon 4B (SEQ ID NO: 2), and PVT1 exon 9 (SEQ ID NO: 1) also have very important research applications. They are very useful for understanding the molecular mechanisms of action of PVT1 exon 4A (SEQ ID NO: 2), PVT1 exon 4B (SEQ ID NO: 3) and PVT1 exon 9 (SEQ ID NO: 1). They are also necessary for performing in vivo tumor studies. No other plasmid vectors expressing these transcripts currently exist. Similarly, the plasmid vectors expressing miR-1205 (SEQ ID NO: 7) and miR-1207-3p (SEQ ID NO: 8) also have important research applications. They are also very useful for understanding the molecular mechanisms of action of miR-1205 (SEQ ID NO: 7) and miR-1207-3p (SEQ ID NO: 8). They are also useful for performing in vivo tumor studies.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

SEQUENCE LISTING

| | |
|---|---|
| <110> | Research Foundation of the City University of New York |
| <120> | PLASMID VECTOR FOR EXPRESSING A PVT1 EXON AND METHOD FOR CONSTRUCTING STANDARD CURVE THEREFOR |
| <130> | 03284.0237US02 |
| <150> | 62/644,023 |
| <151> | 2018-03-16 |
| <160> | 16 |
| <170> | PatentIn version 3.5 |
| <210> | 1 |
| <211> | 273 |
| <212> | DNA |
| <213> | *Homo sapiens* |
| <400> | 1 |

```
gtttttgca tgtctgacac ccatgactcc acctggacct tatggctcca cccagaagca      60
attcagccca acaggaggac agcttcaacc cattacgatt tcatctctgc cccaaccact     120
```

-continued

| SEQUENCE LISTING | |
|---|---|
| cagcagcaag cacctgttac ctgtccaccc ccaccccttc ccccaaactg cctttgaaaa | 180 |
| atccctaacc tatgagcttt gaataagatg agtacgaact tcatcgccca cgtggcgtgg | 240 |
| ccggcctcgt gtctattaaa ttcttttct act | 273 |

<210> 2
<211> 301
<212> DNA
<213> Homo sapiens

<400> 2

| agtctcactc tgtggtccag gctgaagtac agtggcatga tcccaggtca ctgcaacccc | 60 |
|---|---|
| cacctcccgg gttcaagtga tcctcctgcc tcagcctccc gagtagctgg tattacaggc | 120 |
| gtgtgccaca aagcctggct aagttttgta ttttagtag acgggggtt tcaccatgtt | 180 |
| ggccaggttg gtctcgaact cctgacctca agtgatccac tcactttggc ctttcaacgt | 240 |
| gctgggatta caggcgagag tcaccgcacc cggacgactc tgacattttt gaagagtcca | 300 |
| g | 301 |

<210> 3
<211> 130
<212> DNA
<213> Homo sapiens

<400> 3

| aatcctgtta cacctgggat ttaggcactt tcaatctgaa aaaatacata tcctttcagc | 60 |
|---|---|
| actctggacg gacttgagaa ctgtccttac gtgacctaaa gctggagtat tttgagattg | 120 |
| gagaattaag | 130 |

<210> 4
<211> 3015
<212> DNA
<213> Artificial Sequence
<220>
<223> Synthetic vector sold under the brand name pGEM(R)-T Easy

<400> 4

| gggcgaattg ggcccgacgt cgcatgctcc cggccgccat ggcggccgcg ggaattcgat | 60 |
|---|---|
| atcactagtg aattcgcggc cgcctgcagg tcgaccatat gggagagctc ccaacgcgtt | 120 |
| ggatgcatag cttgagtatt ctatagtgtc acctaaatag cttggcgtaa tcatggtcat | 180 |
| agctgtttcc tgtgtgaaat tgttatccgc tcacaattcc acacaacata cgagccggaa | 240 |
| gcataaagtg taaagcctgg ggtgcctaat gagtgagcta actcacatta attgcgttgc | 300 |
| gctcactgcc cgctttccag tcgggaaacc tgtcgtgcca gctgcattaa tgaatcggcc | 360 |
| aacgcgcggg gagaggcggt ttgcgtattg ggcgctcttc cgcttcctcg ctcactgact | 420 |
| cgctgcgctc ggtcgttcgg ctgcggcgag cggtatcagc tcactcaaag gcggtaatac | 480 |
| ggttatccac agaatcaggg gataacgcag gaaagaacat gtgagcaaaa ggccagcaaa | 540 |
| aggccaggaa ccgtaaaaag gccgcgttgc tggcgttttt ccataggctc cgcccccctg | 600 |

-continued

SEQUENCE LISTING

```
acgagcatca caaaaatcga cgctcaagtc agaggtggcg aaacccgaca ggactataaa    660
gataccaggc gtttccccct ggaagctccc tcgtgcgctc tcctgttccg accctgccgc    720
ttaccggata cctgtccgcc tttctccctt cgggaagcgt ggcgctttct catagctcac    780
gctgtaggta tctcagttcg gtgtaggtcg ttcgctccaa gctgggctgt gtgcacgaac    840
cccccgttca gcccgaccgc tgcgccttat ccggtaacta tcgtcttgag tccaacccgg    900
taagacacga cttatcgcca ctggcagcag ccactggtaa caggattagc agagcgaggt    960
atgtaggcgg tgctacagag ttcttgaagt ggtggcctaa ctacggctac actagaagaa   1020
cagtatttgg tatctgcgct ctgctgaagc cagttacctt cggaaaaaga gttggtagct   1080
cttgatccgg caaacaaacc accgctggta gcggtggttt ttttgtttgc aagcagcaga   1140
ttacgcgcag aaaaaaagga tctcaagaag atcctttgat cttttctacg ggtctgacg    1200 ctcagtggaa cgaaaactca cgttaaggga ttttggtcat gagattatca aaaggatct    1260 tcacctagat ccttttaaat taaaatgaa gttttaaatc aatctaaagt atatatgagt    1320
aaacttggtc tgacagttac caatgcttaa tcagtgaggc acctatctca gcgatctgtc    1380
tatttcgttc atccatagtt gcctgactcc ccgtcgtgta gataactacg atacgggagg    1440
gcttaccatc tggccccagt gctgcaatga taccgcgaga cccacgctca ccggctccag    1500
atttatcagc aataaaccag ccagccggaa gggccgagcg cagaagtggt cctgcaactt    1560
tatccgcctc catccagtct attaattgtt gccgggaagc tagagtaagt agttcgccag    1620
ttaatagttt gcgcaacgtt gttgccattg ctacaggcat cgtggtgtca cgctcgtcgt    1680
ttggtatggc ttcattcagc tccggttccc aacgatcaag gcgagttaca tgatccccca    1740
tgttgtgcaa aaaagcggtt agctccttcg gtcctccgat cgttgtcaga agtaagttgg    1800
ccgcagtgtt atcactcatg gttatggcag cactgcataa ttctcttact gtcatgccat    1860
ccgtaagatg cttttctgtg actggtgagt actcaaccaa gtcattctga aatagtgta    1920 tgcggcgacc gagttgctct tgcccggcgt caatacggga taataccgcg ccacatagca    1980
gaactttaaa agtgctcatc attggaaaac gttcttcggg gcgaaaactc tcaaggatct    2040
taccgctgtt gagatccagt tcgatgtaac ccactcgtgc acccaactga tcttcagcat    2100
cttttacttt caccagcgtt tctgggtgag caaaaacagg aaggcaaaat gccgcaaaaa    2160
agggaataag ggcgacacgg aaatgttgaa tactcatact cttccttttt caatattatt    2220
gaagcattta tcaggttat tgtctcatga gcggatacat atttgaatgt atttagaaaa    2280
ataaacaaat aggggttccg cgcacatttc cccgaaaagt gccacctgat gcggtgtgaa    2340
ataccgcaca gatgcgtaag gagaaaatac cgcatcagga aattgtaagc gttaatattt    2400
tgttaaaatt cgcgttaaat ttttgttaaa tcagctcatt ttttaaccaa taggccgaaa    2460
tcggcaaaat cccttataaa tcaaaagaat agaccgagat agggttgagt gttgttccag    2520
tttggaacaa gagtccacta ttaaagaacg tggactccaa cgtcaagggc gaaaaaccg    2580 tctatcaggg cgatggccca ctacgtgaac catcaccta atcaagtttt tggggtcga    2640 ggtgccgtaa agcactaaat cggaacccta aagggagccc ccgatttaga gcttgacggg    2700
gaaagccggc gaacgtggcg agaaaggaag ggaagaaagc gaaggagcg ggcgctaggg    2760 cgctggcaag tgtagcggtc acgctgcgcg taaccaccac acccgccgcg cttaatgcgc    2820
cgctacaggg cgcgtccatt cgccattcag gctgcgcaac tgttgggaag ggcgatcggt    2880
```

-continued

| SEQUENCE LISTING | |
|---|---|
| gcgggcctct tcgctattac gccagctggc gaaaggggga tgtgctgcaa ggcgattaag | 2940 |
| ttgggtaacg ccagggtttt cccagtcacg acgttgtaaa acgacggcca gtgaattgta | 3000 |
| atacgactca ctata | 3015 |
| <210>    5 | |
| <211>    5428 | |
| <212>    DNA | |
| <213>    Artificial Sequence | |
| <220> | |
| <223>    Vector sold under the name pcDNA3.1 | |
| <400>    5 | |
| gacggatcgg gagatctccc gatccctat ggtgcactct cagtacaatc tgctctgatg | 60 |
| ccgcatagtt aagccagtat ctgctccctg cttgtgtgtt ggaggtcgct gagtagtgcg | 120 |
| cgagcaaaat ttaagctaca acaaggcaag gcttgaccga caattgcatg aagaatctgc | 180 |
| ttagggttag gcgttttgcg ctgcttcgcg atgtacgggc cagatatacg cgttgacatt | 240 |
| gattattgac tagttattaa tagtaatcaa ttacggggtc attagttcat agcccatata | 300 |
| tggagttccg cgttacataa cttacggtaa atggcccgcc tggctgaccg cccaacgacc | 360 |
| cccgcccatt gacgtcaata atgacgtatg ttcccatagt aacgccaata gggactttcc | 420 |
| attgacgtca atgggtggag tatttacggt aaactgccca cttggcagta catcaagtgt | 480 |
| atcatatgcc aagtacgccc cctattgacg tcaatgacgg taaatggccc gcctggcatt | 540 |
| atgcccagta catgacctta tgggactttc ctacttggca gtacatctac gtattagtca | 600 |
| tcgctattac catggtgatg cggttttggc agtacatcaa tgggcgtgga tagcggtttg | 660 |
| actcacgggg atttccaagt ctccacccca ttgacgtcaa tgggagtttg ttttggcacc | 720 |
| aaaatcaacg ggactttcca aatgtcgta acaactccgc cccattgacg caaatgggcg | 780 |
| gtaggcgtgt acggtgggag gtctatataa gcagagctct ctggctaact agagaaccca | 840 |
| ctgcttactg gcttatcgaa attaatacga ctcactatag ggagacccaa gctggctagc | 900 |
| gtttaaactt aagcttggta ccgagctcgg atccactagt ccagtgtggt ggaattctgc | 960 |
| agatatccag cacagtggcg gccgctcgag tctagagggc ccgtttaaac ccgctgatca | 1020 |
| gcctcgactg tgccttctag ttgccagcca tctgttgttt gcccctcccc cgtgccttcc | 1080 |
| ttgaccctgg aaggtgccac tcccactgtc ctttcctaat aaaatgagga aattgcatcg | 1140 |
| cattgtctga gtaggtgtca ttctattctg ggggtgggg tggggcagga cagcaagggg | 1200 |
| gaggattggg aagacaatag caggcatgct ggggatgcgg tgggctctat ggcttctgag | 1260 |
| gcggaaagaa ccagctgggg ctctagggg tatcccacg cgccctgtag cggcgcatta | 1320 |
| agcgcggcgg gtgtggtggt tacgcgcagc gtgaccgdta cacttgccag cgccctagcg | 1380 |
| cccgctcctt tcgctttctt cccttccttt ctcgccacgt tcgccggctt tccccgtcaa | 1440 |
| gctctaaatc gggggctccc tttagggttc cgatttagtg ctttacgca cctcgacccc | 1500 |
| aaaaaacttg attagggtga tggttcacgt agtgggccat cgccctgata cggttttt | 1560 |
| cgcccttga cgttggagtc cacgttcttt aatagtggac tcttgttcca aactggaaca | 1620 |
| acactcaacc ctatctcggt ctattctttt gatttataag ggattttgcc gatttcggcc | 1680 |
| tattggttaa aaaatgagct gatttaacaa aaatttaacg cgaattaatt ctgtggaatg | 1740 |

-continued

SEQUENCE LISTING

```
tgtgtcagtt agggtgtgga aagtccccag gctccccagc aggcagaagt atgcaaagca   1800
tgcatctcaa ttagtcagca accaggtgtg gaaagtcccc aggctcccca gcaggcagaa   1860
gtatgcaaag catgcatctc aattagtcag caaccatagt cccgcccta actccgccca    1920 tcccgcccct aactccgccc agttccgccc attctccgcc ccatggctga ctaattttt    1980 ttatttatgc agaggccgag gccgcctctg cctctgagct attccagaag tagtgaggag   2040
gcttttttgg aggcctaggc ttttgcaaaa agctcccggg agcttgtata tccattttcg   2100
gatctgatca agagacagga tgaggatcgt ttcgcatgat tgaacaagat ggattgcacg   2160
caggttctcc ggccgcttgg gtggagaggc tattcggcta tgactgggca acagacaa    2220 tcggctgctc tgatgccgcc gtgttccggc tgtcagcgca ggggcgcccg gttctttttg   2280
tcaagaccga cctgtccggt gccctgaatg aactgcagga cgaggcagcg cggctatcgt   2340
ggctggccac gacgggcgtt ccttgcgcag ctgtgctcga cgttgtcact gaagcgggaa   2400
gggactggct gctattgggc gaagtgccgg ggcaggatct cctgtcatct caccttgctc   2460
ctgccgagaa agtatccatc atggctgatg caatgcggcg gctgcatacg cttgatccgg   2520
ctacctgccc attcgaccac caagcgaaac atcgcatcga gcgagcacgt actcggatgg   2580
aagccggtct tgtcgatcag gatgatctgg acgaagagca tcaggggctc gcgccagccg   2640
aactgttcgc caggctcaag gcgcgcatgc ccgacggcga ggatctcgtc gtgacccatg   2700
gcgatgcctg cttgccgaat atcatggtgg aaaatggccg cttttctgga ttcatcgact   2760
gtggccggct gggtgtggcg gaccgctatc aggacatagc gttggctacc cgtgatattg   2820
ctgaagagct tggcggcgaa tgggctgacc gcttcctcgt gctttacggt atcgccgctc   2880
ccgattcgca gcgcatcgcc ttctatcgcc ttcttgacga gttcttctga gcgggactct   2940
ggggttcgaa atgaccgacc aagcgacgcc caacctgcca tcacgagatt tcgattccac   3000
cgccgccttc tatgaaaggt tgggcttcgg aatcgttttc cgggacgccg gctggatgat   3060
cctccagcgc ggggatctca tgctggagtt cttcgcccac cccaacttgt ttattgcagc   3120
ttataatggt tacaaataaa gcaatagcat cacaaatttc acaaataaag catttttttc   3180
actgcattct agttgtggtt tgtccaaact catcaatgta tcttatcatg tctgtatacc   3240
gtcgacctct agctagagct tggcgtaatc atggtcatag ctgtttcctg tgtgaaattg   3300
ttatccgctc acaattccac acaacatacg agccggaagc ataaagtgta aagcctgggg   3360
tgcctaatga gtgagctaac tcacattaat tgcgttgcgc tcactgcccg ctttccagtc   3420
gggaaacctg tcgtgccagc tgcattaatg aatcggccaa cgcgcgggga gaggcggttt   3480
gcgtattggg cgctcttccg cttcctcgct cactgactcg ctgcgctcgg tcgttcggct   3540
gcggcgagcg gtatcagctc actcaaaggc ggtaatacgg ttatccacag aatcaggga    3600 taacgcagga aagaacatgt gagcaaaagg ccagcaaaag gccaggaacc gtaaaaaggc   3660
cgcgttgctg gcgttttcc ataggctccg ccccctgac gagcatcaca aaaatcgacg     3720
ctcaagtcag aggtggcgaa acccgacagg actataaaga taccaggcgt ttccccctgg   3780
aagctccctc gtgcgctctc ctgttccgac cctgccgctt accggatacc tgtccgcctt   3840
tctcccttcg ggaagcgtgg cgctttctca tagctcacgc tgtaggtatc tcagttcggt   3900
gtaggtcgtt cgctccaagc tgggctgtgt gcacgaaccc cccgttcagc ccgaccgctg   3960
cgccttatcc ggtaactatc gtcttgagtc aacccggta agacacgact tatcgccact   4020
```

-continued

| SEQUENCE LISTING |
|---|

```
ggcagcagcc actggtaaca ggattagcag agcgaggtat gtaggcggtg ctacagagtt      4080
cttgaagtgg tggcctaact acggctacac tagaagaaca gtatttggta tctgcgctct      4140
gctgaagcca gttaccttcg gaaaaagagt tggtagctct tgatccggca aacaaaccac      4200
cgctggtagc ggtttttttg tttgcaagca gcagattacg cgcagaaaaa aaggatctca      4260
agaagatcct ttgatctttt ctacggggtc tgacgctcag tggaacgaaa actcacgtta      4320
agggattttg gtcatgagat tatcaaaaag gatcttcacc tagatccttt taaattaaaa      4380
atgaagtttt aaatcaatct aaagtatata tgagtaaact tggtctgaca gttaccaatg      4440
cttaatcagt gaggcaccta tctcagcgat ctgtctattt cgttcatcca tagttgcctg      4500
actccccgtc gtgtagataa ctacgatacg ggagggctta ccatctggcc ccagtgctgc      4560
aatgataccg cgagacccac gctcaccggc tccagattta tcagcaataa accagccagc      4620
cggaagggcc gagcgcagaa gtggtcctgc aactttatcc gcctccatcc agtctattaa      4680
ttgttgccgg gaagctagag taagtagttc gccagttaat agtttgcgca acgttgttgc      4740
cattgctaca ggcatcgtgg tgtcacgctc gtcgtttggt atggcttcat tcagctccgg      4800
ttcccaacga tcaaggcgag ttacatgatc ccccatgttg tgcaaaaaag cggttagctc      4860
cttcggtcct ccgatcgttg tcagaagtaa gttggccgca gtgttatcac tcatggttat      4920
ggcagcactg cataattctc ttactgtcat gccatccgta agatgctttt ctgtgactgg      4980
tgagtactca accaagtcat tctgagaata gtgtatgcgg cgaccgagtt gctcttgccc      5040
ggcgtcaata cgggataata ccgcgccaca tagcagaact ttaaaagtgc tcatcattgg      5100
aaaacgttct cggggcgaaa actctcaag gatcttaccg ctgttgagat ccagttcgat      5160
gtaacccact cgtgcaccca actgatcttc agcatctttt actttcacca gcgtttctgg      5220
gtgagcaaaa acaggaaggc aaaatgccgc aaaaaaggga ataagggcga cacggaaatg      5280
ttgaatactc atactcttcc tttttcaata ttattgaagc atttatcagg gttattgtct      5340
catgagcgga tacatatttg aatgtattta gaaaaataaa caaatagggg ttccgcgcac      5400
atttccccga aaagtgccac ctgacgtc                                         5428
```

<210> 6
<211> 344
<212> DNA
<213> Artificial Sequence
<220>
<223> Vector sold under the brand name miRNASelect(TM) pEGP-miR
<400> 6

```
cgattagttc tcgaggatcc gactgttctt ttccctcatt acacaggaaa ccggaattac       60
aaaggagaac ggcttcctgt gatgctcagc tgtgattact ttcaacattc accctggatg      120
ttctcttcac tgtgggatga ggtagtaggt tgtatagttt tagggtcaca cccaccactg      180
ggagataact atacaatcta ctgtctttcc taaggtgatg gaaagtctg cattcatggg      240 gtctcatagg aaaccaagaa caaactgcag tgttttaaag tatatcttgc cttaaaagca      300
tttgcttatg ctatgcatga agtcgctagc tcgagctttt ggag                       344
```

<210> 7
<211> 22

SEQUENCE LISTING

<212> RNA

<213> Artificial Sequence

<220>

<223> Synthetic mature strand miR-1205

<220>

<221> misc_feature

<222> (21)..(22)

<223> n is a, c, g, or u

<400> 7
ucugcagggu uugcuuugag nn                                              22

<210> 8

<211> 20

<212> RNA

<213> Artificial Sequence

<220>

<223> Synthetic mature sequence miRNA-1207-3p

<220>

<221> misc_feature

<222> (19)..(20)

<223> n is a, c, g, or u

<400> 8
ucagcuggcc cucauuucnn                                                 20

<210> 9

<211> 21

<212> DNA

<213> Artificial Sequence

<220>

<223> PVT1 exon 9 PGEMT reverse primer

<400> 9
agtagaaaaa gaatttaata g                                               21

<210> 10

<211> 30

<212> DNA

<213> Artificial Sequence

<220>

<223> att AAGCTT GTT TTT TGC ATG TCT GAC ACC

<400> 10
attaagcttg tttttgcat gtctgacacc                                       30

SEQUENCE LISTING

| | | |
|---|---|---|
| <210> | 11 | |
| <211> | 30 | |
| <212> | DNA | |
| <213> | Artificial Sequence | |
| <220> | | |
| <223> | pcDNA 3.1 exon 9 PCDNA Reverse primer | |
| <400> | 11 | | attggatcca gtagaaaaag aatttaatag 30

| | | |
|---|---|---|
| <210> | 12 | |
| <211> | 30 | |
| <212> | DNA | |
| <213> | Artificial Sequence | |
| <220> | | |
| <223> | pcDNA 3.1 exon 4A PCDNA Forward primer | |
| <400> | 12 | | attaagctta gtctcactct gtggtccagg 30

| | | |
|---|---|---|
| <210> | 13 | |
| <211> | 30 | |
| <212> | DNA | |
| <213> | Artificial Sequence | |
| <220> | | |
| <223> | pcDNA3.1 exon 4A PCDNA Reverse primer | |
| <400> | 13 | | attggatccc tggactcttc aaaaatgtca 30

| | | |
|---|---|---|
| <210> | 14 | |
| <211> | 30 | |
| <212> | DNA | |
| <213> | Artificial Sequence | |
| <220> | | |
| <223> | pcDNA3.1 exon 4B PCDNA Forward primer | |
| <400> | 14 | | attaagctta atcctgttac acctgggatt 30

| | | |
|---|---|---|
| <210> | 15 | |
| <211> | 30 | |
| <212> | DNA | |
| <213> | Artificial Sequence | |
| <220> | | |
| <223> | pcDNA3.1 exon 4B PCDNA Reverse primer | |
| <400> | 15 | |

SEQUENCE LISTING

```
attggatccc ttaattctcc aatctcaaaa                                      30
```

<210> 16
<211> 21
<212> DNA
<213> Artificial Sequence
<220>
<223> PVT1 exon 9 p-GEMT Forward primer
<400> 16

```
gtttttgca tgtctgacac c                                                21
```

SEQUENCE LISTING

<160> NUMBER OF SEQ ID NOS: 16

<210> SEQ ID NO 1
<211> LENGTH: 273
<212> TYPE: DNA
<213> ORGANISM: Homo sapiens

<400> SEQUENCE: 1

```
gtttttgca tgtctgacac ccatgactcc acctggacct tatggctcca cccagaagca      60
attcagccca acaggaggac agcttcaacc cattacgatt tcatctctgc cccaaccact    120
cagcagcaag cacctgttac ctgtccaccc ccaccccttc ccccaaactg cctttgaaaa    180
atccctaacc tatgagcttt gaataagatg agtacgaact tcatcgccca cgtggcgtgg    240
ccggcctcgt gtctattaaa ttcttttttct act                                273
```

<210> SEQ ID NO 2
<211> LENGTH: 301
<212> TYPE: DNA
<213> ORGANISM: Homo sapiens

<400> SEQUENCE: 2

```
agtctcactc tgtggtccag gctgaagtac agtggcatga tcccaggtca ctgcaacccc     60
cacctcccgg gttcaagtga tcctcctgcc tcagcctccc gagtagctgg tattacaggc    120
gtgtgccaca aagcctggct aagttttgta ttttttagtag acacggggtt tcaccatgtt   180
ggccaggttg gtctcgaact cctgacctca agtgatccac tcactttggc ctttcaacgt    240
gctgggatta caggcgagag tcaccgcacc cggacgactc tgacattttt gaagagtcca    300
g                                                                    301
```

<210> SEQ ID NO 3
<211> LENGTH: 130
<212> TYPE: DNA
<213> ORGANISM: Homo sapiens

<400> SEQUENCE: 3

```
aatcctgtta cacctgggat ttaggcactt tcaatctgaa aaaatacata tcctttcagc     60
actctggacg gacttgagaa ctgtccttac gtgacctaaa gctggagtat tttgagattg    120
gagaattaag                                                           130
```

<210> SEQ ID NO 4
<211> LENGTH: 3015
<212> TYPE: DNA
<213> ORGANISM: Artificial Sequence
<220> FEATURE:
<223> OTHER INFORMATION: Synthetic vector sold under the brand name
      pGEM(R)-T Easy

<400> SEQUENCE: 4

```
gggcgaattg ggcccgacgt cgcatgctcc cggccgccat ggcggccgcg ggaattcgat      60
atcactagtg aattcgcggc cgcctgcagg tcgaccatat gggagagctc ccaacgcgtt     120
ggatgcatag cttgagtatt ctatagtgtc acctaaatag cttggcgtaa tcatggtcat     180
agctgtttcc tgtgtgaaat tgttatccgc tcacaattcc acacaacata cgagccggaa     240
gcataaagtg taaagcctgg ggtgcctaat gagtgagcta actcacatta attgcgttgc     300
gctcactgcc cgctttccag tcgggaaacc tgtcgtgcca gctgcattaa tgaatcggcc     360
aacgcgcggg gagaggcggt ttgcgtattg ggcgctcttc cgcttcctcg ctcactgact     420
cgctgcgctc ggtcgttcgg ctgcggcgag cggtatcagc tcactcaaag gcggtaatac     480
ggttatccac agaatcaggg gataacgcag gaaagaacat gtgagcaaaa ggccagcaaa     540
aggccaggaa ccgtaaaaag gccgcgttgc tggcgttttt ccataggctc cgcccccctg     600
acgagcatca caaaaatcga cgctcaagtc agaggtggcg aaacccgaca ggactataaa     660
gataccaggc gtttccccct ggaagctccc tcgtgcgctc tcctgttccg accctgccgc     720
ttaccggata cctgtccgcc tttctccctt cgggaagcgt ggcgctttct catagctcac     780
gctgtaggta tctcagttcg gtgtaggtcg ttcgctccaa gctgggctgt gtgcacgaac     840
cccccgttca gcccgaccgc tgcgccttat ccggtaacta tcgtcttgag tccaacccgg     900
taagacacga cttatcgcca ctggcagcag ccactggtaa caggattagc agagcgaggt     960
atgtaggcgg tgctacagag ttcttgaagt ggtggcctaa ctacggctac actagaagaa    1020
cagtatttgg tatctgcgct ctgctgaagc cagttacctt cggaaaaaga gttggtagct    1080
cttgatccgg caaacaaacc accgctggta gcggtggttt ttttgtttgc aagcagcaga    1140
ttacgcgcag aaaaaaagga tctcaagaag atcctttgat cttttctacg gggtctgacg    1200
ctcagtggaa cgaaaactca cgttaaggga ttttggtcat gagattatca aaaaggatct    1260
tcacctagat ccttttaaat taaaaatgaa gttttaaatc aatctaaagt atatatgagt    1320
aaacttggtc tgacagttac caatgcttaa tcagtgaggc acctatctca gcgatctgtc    1380
tatttcgttc atccatagtt gcctgactcc ccgtcgtgta gataactacg atacgggagg    1440
gcttaccatc tggccccagt gctgcaatga taccgcgaga cccacgctca ccggctccag    1500
atttatcagc aataaaccag ccagccggaa gggccgagcg cagaagtggt cctgcaactt    1560
tatccgcctc catccagtct attaattgtt gccgggaagc tagagtaagt agttcgccag    1620
ttaatagttt gcgcaacgtt gttgccattg ctacaggcat cgtggtgtca cgctcgtcgt    1680
ttggtatggc ttcattcagc tccggttccc aacgatcaag gcgagttaca tgatccccca    1740
tgttgtgcaa aaaagcggtt agctccttcg gtcctccgat cgttgtcaga agtaagttgg    1800
ccgcagtgtt atcactcatg gttatggcag cactgcataa ttctcttact gtcatgccat    1860
ccgtaagatg cttttctgtg actggtgagt actcaaccaa gtcattctga atagtgta     1920
tgcggcgacc gagttgctct tgcccggcgt caatacggga taataccgcg ccacatagca    1980
gaactttaaa agtgctcatc attggaaaac gttcttcggg gcgaaaactc tcaaggatct    2040
```

```
taccgctgtt gagatccagt tcgatgtaac ccactcgtgc acccaactga tcttcagcat   2100
cttttacttt caccagcgtt tctgggtgag caaaaacagg aaggcaaaat gccgcaaaaa   2160
agggaataag ggcgacacgg aaatgttgaa tactcatact cttcctttttt caatattatt   2220 gaagcattta tcaggggttat tgtctcatga gcggatacat atttgaatgt atttagaaaa   2280
ataaacaaat aggggttccg cgcacatttc cccgaaaagt gccacctgat gcggtgtgaa   2340
ataccgcaca gatgcgtaag gagaaaatac cgcatcagga aattgtaagc gttaatattt   2400
tgttaaaatt cgcgttaaat ttttgttaaa tcagctcatt ttttaaccaa taggccgaaa   2460
tcggcaaaat cccttataaa tcaaaagaat agaccgagat agggttgagt gttgttccag   2520
tttggaacaa gagtccacta ttaaagaacg tggactccaa cgtcaaaggg cgaaaaaccg   2580
tctatcaggg cgatggccca ctacgtgaac catcaccctaa atcaagtttt ttggggtcga   2640
ggtgccgtaa agcactaaat cggaacccta aagggagccc ccgatttaga gcttgacggg   2700
gaaagccggc gaacgtggcg agaaaggaag ggaagaaagc gaaaggagcg ggcgctaggg   2760
cgctggcaag tgtagcggtc acgctgcgcg taaccaccac acccgccgcg cttaatgcgc   2820
cgctacaggg cgcgtccatt cgccattcag gctgcgcaac tgttgggaag ggcgatcggt   2880
gcgggcctct tcgctattac gccagctggc gaaagggggga tgtgctgcaa ggcgattaag   2940
ttgggtaacg ccagggtttt cccagtcacg acgttgtaaa acgacggcca gtgaattgta   3000
atacgactca ctata   3015
```

<210> SEQ ID NO 5
<211> LENGTH: 5428
<212> TYPE: DNA
<213> ORGANISM: Artificial Sequence
<220> FEATURE:
<223> OTHER INFORMATION: Vector sold under the name pcDNA3.1

<400> SEQUENCE: 5

```
gacggatcgg gagatctccc gatcccctat ggtgcactct cagtacaatc tgctctgatg    60
ccgcatagtt aagccagtat ctgctccctg cttgtgtgtt ggaggtcgct gagtagtgcg   120
cgagcaaaat ttaagctaca acaaggcaag gcttgaccga caattgcatg aagaatctgc   180
ttagggttag gcgttttgcg ctgcttcgcg atgtacgggc cagatatacg cgttgacatt   240
gattattgac tagttattaa tagtaatcaa ttacggggtc attagttcat agcccatata   300
tggagttccg cgttacataa cttacggtaa atggcccgcc tggctgaccg cccaacgacc   360
cccgcccatt gacgtcaata atgacgtatg ttcccatagt aacgccaata gggactttcc   420
attgacgtca atgggtggag tatttacggt aaactgccca cttggcagta catcaagtgt   480
atcatatgcc aagtacgccc cctattgacg tcaatgacgg taaatggccc gcctggcatt   540
atgcccagta catgacctta tgggactttc ctacttggca gtacatctac gtattagtca   600
tcgctattac catggtgatg cggttttggc agtacatcaa tgggcgtgga tagcggtttg   660
actcacgggg atttccaagt ctccacccca ttgacgtcaa tgggagtttg ttttggcacc   720
aaaatcaacg ggactttcca aaatgtcgta acaactccgc cccattgacg caaatgggcg   780
gtaggcgtgt acggtgggag gtctatataa gcagagctct ctggctaact agagaaccca   840
ctgcttactg gcttatcgaa attaatacga ctcactatag ggagacccaa gctggctagc   900
gtttaaactt aagcttggta ccgagctcgg atccactagt ccagtgtggt ggaattctgc   960
agatatccag cacagtggcg gccgctcgag tctagagggc ccgtttaaac ccgctgatca   1020
```

```
gcctcgactg tgccttctag ttgccagcca tctgttgttt gcccctcccc cgtgccttcc      1080
ttgaccctgg aaggtgccac tcccactgtc ctttcctaat aaaatgagga aattgcatcg      1140
cattgtctga gtaggtgtca ttctattctg ggggtgggg tggggcagga cagcaagggg       1200
gaggattggg aagacaatag caggcatgct gggatgcgg tgggctctat ggcttctgag       1260
gcggaaagaa ccagctgggg ctctaggggg tatccccacg cgccctgtag cggcgcatta      1320
agcgcggcgg gtgtggtggt tacgcgcagc gtgaccgcta cacttgccag cgccctagcg      1380
cccgctcctt tcgctttctt cccttccttt ctcgccacgt tcgccggctt tccccgtcaa      1440
gctctaaatc gggggctccc tttagggttc cgatttagtg ctttacggca cctcgacccc      1500
aaaaaacttg attagggtga tggttcacgt agtgggccat cgccctgata cggttttt       1560 cgccctttga cgttggagtc cacgttcttt aatagtggac tcttgttcca aactggaaca      1620
acactcaacc ctatctcggt ctattctttt gatttataag ggattttgcc gatttcggcc      1680
tattggttaa aaaatgagct gatttaacaa aaatttaacg cgaattaatt ctgtggaatg      1740
tgtgtcagtt agggtgtgga aagtccccag gctccccagc aggcagaagt atgcaaagca      1800
tgcatctcaa ttagtcagca accaggtgtg gaaagtcccc aggctcccca gcaggcagaa      1860
gtatgcaaag catgcatctc aattagtcag caaccatagt cccgccccta actccgccca      1920
tcccgcccct aactccgccc agttccgccc attctccgcc ccatggctga ctaattttt      1980 ttatttatgc agaggccgag gccgcctctg cctctgagct attccagaag tagtgaggag      2040
gcttttttgg aggcctaggc ttttgcaaaa agctcccggg agcttgtata tccatttcg      2100 gatctgatca agagacagga tgaggatcgt ttcgcatgat tgaacaagat ggattgcacg      2160
caggttctcc ggccgcttgg gtggagaggc tattcggcta tgactgggca acagacaa       2220 tcggctgctc tgatgccgcc gtgttccggc tgtcagcgca gggcgcccg gttctttttg       2280 tcaagaccga cctgtccggt gccctgaatg aactgcagga cgaggcagcg cggctatcgt      2340
ggctggccac gacgggcgtt ccttgcgcag ctgtgctcga cgttgtcact gaagcgggaa      2400
gggactggct gctattgggc gaagtgccgg ggcaggatct cctgtcatct caccttgctc      2460
ctgccgagaa agtatccatc atggctgatg caatgcggcg gctgcatacg cttgatccgg      2520
ctacctgccc attcgaccac caagcgaaac atcgcatcga gcgagcacgt actcggatgg      2580
aagccggtct tgtcgatcag gatgatctgg acgaagagca tcaggggctc gcgccagccg      2640
aactgttcgc caggctcaag gcgcgcatgc ccgacggcga ggatctcgtc gtgacccatg      2700
gcgatgcctg cttgccgaat atcatggtgg aaaatggccg cttttctgga ttcatcgact      2760
gtggccggct gggtgtggcg gaccgctatc aggacatagc gttggctacc cgtgatattg      2820
ctgaagagct tggcggcgaa tgggctgacc gcttcctcgt gctttacggt atcgccgctc      2880
ccgattcgca gcgcatcgcc ttctatcgcc ttcttgacga gttcttctga gcgggactct      2940
ggggttcgaa atgaccgacc aagcgacgcc caacctgcca tcacgagatt tcgattccac      3000
cgccgccttc tatgaaaggt tgggcttcgg aatcgttttc cgggacgccg gctggatgat      3060
cctccagcgc ggggatctca tgctggagtt cttcgcccac cccaacttgt ttattgcagc      3120
ttataatggt tacaaataaa gcaatagcat cacaaatttc acaaataaag catttttttc      3180
actgcattct agttgtggtt tgtccaaact catcaatgta tcttatcatg tctgtatacc      3240
gtcgacctct agctagagct tggcgtaatc atggtcatag ctgtttcctg tgtgaaattg      3300
ttatccgctc acaattccac acaacatacg agccggaagc ataaagtgta aagcctgggg      3360
tgcctaatga gtgagctaac tcacattaat tgcgttgcgc tcactgcccg ctttccagtc      3420
```

-continued

```
gggaaacctg tcgtgccagc tgcattaatg aatcggccaa cgcgcgggga gaggcggttt    3480
gcgtattggg cgctcttccg cttcctcgct cactgactcg ctgcgctcgg tcgttcggct    3540
gcggcgagcg gtatcagctc actcaaaggc ggtaatacgg ttatccacag aatcagggga    3600
taacgcagga aagaacatgt gagcaaaagg ccagcaaaag gccaggaacc gtaaaaaggc    3660
cgcgttgctg gcgttttttcc ataggctccg cccccctgac gagcatcaca aaaatcgacg    3720
ctcaagtcag aggtggcgaa acccgacagg actataaaga taccaggcgt ttccccctgg    3780
aagctccctc gtgcgctctc ctgttccgac cctgccgctt accggatacc tgtccgcctt    3840
tctcccttcg ggaagcgtgg cgctttctca tagctcacgc tgtaggtatc tcagttcggt    3900
gtaggtcgtt cgctccaagc tgggctgtgt gcacgaaccc cccgttcagc ccgaccgctg    3960
cgccttatcc ggtaactatc gtcttgagtc caacccggta agacacgact tatcgccact    4020
ggcagcagcc actggtaaca ggattagcag agcgaggtat gtaggcggtg ctacagagtt    4080
cttgaagtgg tggcctaact acggctacac tagaagaaca gtatttggta tctgcgctct    4140
gctgaagcca gttaccttcg gaaaaagagt tggtagctct tgatccggca aacaaaccac    4200
cgctggtagc ggtttttttg tttgcaagca gcagattacg cgcagaaaaa aaggatctca    4260
agaagatcct ttgatctttt ctacggggtc tgacgctcag tggaacgaaa actcacgtta    4320
agggattttg gtcatgagat tatcaaaaag gatcttcacc tagatccttt taaattaaaa    4380
atgaagtttt aaatcaatct aaagtatata tgagtaaact tggtctgaca gttaccaatg    4440
cttaatcagt gaggcaccta tctcagcgat ctgtctattt cgttcatcca tagttgcctg    4500
actccccgtc gtgtagataa ctacgatacg ggagggctta ccatctggcc ccagtgctgc    4560
aatgataccg cgagacccac gctcaccggc tccagattta tcagcaataa accagccagc    4620
cggaagggcc gagcgcagaa gtggtcctgc aactttatcc gcctccatcc agtctattaa    4680
ttgttgccgg gaagctagag taagtagttc gccagttaat agtttgcgca acgttgttgc    4740
cattgctaca ggcatcgtgg tgtcacgctc gtcgtttggt atggcttcat tcagctccgg    4800
ttcccaacga tcaaggcgag ttacatgatc ccccatgttg tgcaaaaaag cggttagctc    4860
cttcggtcct ccgatcgttg tcagaagtaa gttggccgca gtgttatcac tcatggttat    4920
ggcagcactg cataattctc ttactgtcat gccatccgta agatgctttt ctgtgactgg    4980
tgagtactca accaagtcat tctgagaata gtgtatgcgg cgaccgagtt gctcttgccc    5040
ggcgtcaata cgggataata ccgcgccaca tagcagaact ttaaaagtgc tcatcattgg    5100
aaaacgttct cggggcgaa aactctcaag gatcttaccg ctgttgagat ccagttcgat    5160
gtaacccact cgtgcaccca actgatcttc agcatctttt actttcacca gcgtttctgg    5220
gtgagcaaaa acaggaaggc aaaatgccgc aaaaaaggga ataagggcga cacggaaatg    5280
ttgaatactc atactcttcc tttttcaata ttattgaagc atttatcagg gttattgtct    5340
catgagcgga tacatatttg aatgtattta gaaaaataaa caaatagggg ttccgcgcac    5400
atttccccga aaagtgccac ctgacgtc                                       5428
```

<210> SEQ ID NO 6
<211> LENGTH: 344
<212> TYPE: DNA
<213> ORGANISM: Artificial Sequence
<220> FEATURE:
<223> OTHER INFORMATION: Vector sold under the brand name
      miRNASelect(TM) pEGP-miR

<400> SEQUENCE: 6

```
cgattagttc tcgaggatcc gactgttctt ttccctcatt acacaggaaa ccggaattac    60
aaaggagaac ggcttcctgt gatgctcagc tgtgattact ttcaacattc accctggatg   120
ttctcttcac tgtgggatga ggtagtaggt tgtatagttt tagggtcaca cccaccactg   180
ggagataact atacaatcta ctgtctttcc taaggtgatg gaaaagtctg cattcatggg   240
gtctcatagg aaaccaagaa caaactgcag tgttttaaag tatatcttgc cttaaaagca   300
tttgcttatg ctatgcatga agtcgctagc tcgagctttt ggag                    344
```

<210> SEQ ID NO 7
<211> LENGTH: 22
<212> TYPE: RNA
<213> ORGANISM: Artificial Sequence
<220> FEATURE:
<223> OTHER INFORMATION: Synthetic mature strand miR-1205
<220> FEATURE:
<221> NAME/KEY: misc_feature
<222> LOCATION: (21)..(22)
<223> OTHER INFORMATION: n is a, c, g, or u

<400> SEQUENCE: 7
ucugcagggu uugcuuugag nn                                              22

<210> SEQ ID NO 8
<211> LENGTH: 20
<212> TYPE: RNA
<213> ORGANISM: Artificial Sequence
<220> FEATURE:
<223> OTHER INFORMATION: Synthetic mature sequence miRNA-1207-3p
<220> FEATURE:
<221> NAME/KEY: misc_feature
<222> LOCATION: (19)..(20)
<223> OTHER INFORMATION: n is a, c, g, or u

<400> SEQUENCE: 8
ucagcuggcc cucauuucnn                                                 20

<210> SEQ ID NO 9
<211> LENGTH: 21
<212> TYPE: DNA
<213> ORGANISM: Artificial Sequence
<220> FEATURE:
<223> OTHER INFORMATION: PVT1 exon 9 PGEMT reverse primer

<400> SEQUENCE: 9
agtagaaaaa gaatttaata g                                               21

<210> SEQ ID NO 10
<211> LENGTH: 30
<212> TYPE: DNA
<213> ORGANISM: Artificial Sequence
<220> FEATURE:
<223> OTHER INFORMATION: att AAGCTT GTT TTT TGC ATG TCT GAC ACC

<400> SEQUENCE: 10
attaagcttg tttttttgcat gtctgacacc                                     30

<210> SEQ ID NO 11
<211> LENGTH: 30
<212> TYPE: DNA
<213> ORGANISM: Artificial Sequence
<220> FEATURE:
<223> OTHER INFORMATION: pcDNA 3.1 exon 9 PCDNA Reverse primer

<400> SEQUENCE: 11

-continued

```
attggatcca gtagaaaaag aatttaatag                                    30

<210> SEQ ID NO 12
<211> LENGTH: 30
<212> TYPE: DNA
<213> ORGANISM: Artificial Sequence
<220> FEATURE:
<223> OTHER INFORMATION: pcDNA 3.1 exon 4A PCDNA Forward primer

<400> SEQUENCE: 12
attaagctta gtctcactct gtggtccagg                                    30

<210> SEQ ID NO 13
<211> LENGTH: 30
<212> TYPE: DNA
<213> ORGANISM: Artificial Sequence
<220> FEATURE:
<223> OTHER INFORMATION: pcDNA3.1 exon 4A PCDNA Reverse primer

<400> SEQUENCE: 13
attggatccc tggactcttc aaaaatgtca                                    30

<210> SEQ ID NO 14
<211> LENGTH: 30
<212> TYPE: DNA
<213> ORGANISM: Artificial Sequence
<220> FEATURE:
<223> OTHER INFORMATION: pcDNA3.1 exon 4B PCDNA Forward primer

<400> SEQUENCE: 14
attaagctta atcctgttac acctgggatt                                    30

<210> SEQ ID NO 15
<211> LENGTH: 30
<212> TYPE: DNA
<213> ORGANISM: Artificial Sequence
<220> FEATURE:
<223> OTHER INFORMATION: pcDNA3.1 exon 4B PCDNA Reverse primer

<400> SEQUENCE: 15
attggatccc ttaattctcc aatctcaaaa                                    30

<210> SEQ ID NO 16
<211> LENGTH: 21
<212> TYPE: DNA
<213> ORGANISM: Artificial Sequence
<220> FEATURE:
<223> OTHER INFORMATION: PVT1 exon 9 p-GEMT Forward primer

<400> SEQUENCE: 16
gttttttgca tgtctgacac c                                             21
```

What is claimed is:

1. A plasmid vector comprising:
   a vector consisting of:
   (1) DNA segment selected from a group consisting of plasmacytoma variant translocation 1 exon 9 (PVT1 exon 9, SEQ ID NO: 1), plasmacytoma variant translocation 1 exon 4A (PVT1 exon 4A, SEQ ID NO: 2) and plasmacytoma variant translocation 1 (PVT1 exon 4B, SEQ ID NO: 3); and
   (2) a plasmid vector that is SEQ ID NO: 4 or SEQ ID NO: 5; and
   (3) a corresponding complementary strand that is complementary to both the DNA segment and the plasmid vector.

2. A method for cloning an exon into a plasmid vector, the method comprising:
   ligating the exon into a plasmid vector selected from a group consisting of SEQ ID NO: 4 and SEQ ID NO: 5, wherein the exon consists of:
   (1) a mature strand, and a corresponding complementary strand, wherein the mature strand is selected from a group consisting of plasmacytoma variant translocation 1 exon 9 (PVT1 exon 9, SEQ ID NO: 1), plasmacytoma variant translocation 1 exon 4A (PVT1 exon 4A, SEQ ID NO: 2), plasmacytoma variant translocation 1 (PVT1 exon 4B, SEQ ID NO: 3)
   transforming the plasmid vector into *Escherichia coli* (*E. coli*);

selecting at least one colony of the *Escherichia coli* (*E. coli*) that successfully transformed the plasmid vector into the *Escherichia coli* (*E. coli*).

3. The method as recited in claim 2, wherein the exon is PVT1 exon 9 (SEQ ID NO: 1) and the plasmid vector is SEQ ID NO: 4 and a corresponding complementary strand that is complementary to both the exon and the plasmid vector.

4. The method as recited in claim 3, wherein the exon is a blunt-ended exon.

5. The method as recited in claim 4, wherein the exon has a 3' A-tail.

6. The method as recited in claim 3, wherein the exon was generated by performing polymerase chain reaction (PCR) using forward and reverse primers consisting of SEQ ID NO: 9 and SEQ ID NO: 16.

7. The method as recited in claim 2, wherein the exon is PVT1 exon 4A (SEQ ID NO: 2) the plasmid vector is SEQ ID NO: 5 and the corresponding complementary strand.

8. The method as recited in claim 7, wherein the step of transforming is preceded by a step of administering a restriction enzyme to both the exon and the plasmid vector.

9. The method as recited in claim 8, wherein the restriction enzyme is selected from a group consisting of HindIII and BamHI.

10. The method as recited in claim 7, wherein the exon was generated by performing polymerase chain reaction (PCR) using forward and reverse primers consisting of SEQ ID NO: 12 and SEQ ID NO: 13.

11. The method as recited in claim 2, wherein the exon is PVT1 exon 4B (SEQ ID NO: 3) the plasmid vector is SEQ ID NO: 5 and the corresponding complementary strand.

12. The method as recited in claim 11, wherein the step of transforming is preceded by a step of administering a restriction enzyme to both the exon and the plasmid vector.

13. The method as recited in claim 12, wherein the restriction enzyme is selected from a group consisting of HindIII and BamHI.

14. The method as recited in claim 11, wherein the exon was generated by performing polymerase chain reaction (PCR) using forward and reverse primers consisting of SEQ ID NO: 14 and SEQ ID NO: 15.

15. The method as recited in claim 2, further comprising linearizing the cloned plasmids;
quantifying a number of the cloned plasmids;
performing serial dilutions on the cloned plasmids to produce a plurality of samples with known concentrations of the cloned plasmids;
recording a spectral absorbance of each sample in the plurality of samples;
constructing a standard curve that correlates the spectra absorbance with the known concentrations.

* * * * *